(12) United States Patent
Lochmann et al.

(10) Patent No.: US 12,091,383 B2
(45) Date of Patent: Sep. 17, 2024

(54) METHOD FOR PRODUCING LIPIDS COMPRISING STRUCTURAL UNITS BASED ON GLYCERIDES OF HYDROXYCARBOXYLC ACIDS

(71) Applicant: IOI Oleo GmbH, Witten (DE)

(72) Inventors: Dirk Lochmann, Witten (DE); Sebastian Reyer, Witten (DE); Michael Stehr, Witten (DE)

(73) Assignee: KETOLIPIX THERAPEUTICS GMBH (DE)

( * ) Notice: Subject to any disclaimer, the term of this patent is extended or adjusted under 35 U.S.C. 154(b) by 201 days.

(21) Appl. No.: 17/378,962

(22) PCT Filed: Jan. 23, 2019

(86) PCT No.: PCT/EP2019/051541
§ 371 (c)(1),
(2) Date: Jul. 19, 2021

(87) PCT Pub. No.: WO2020/147980
PCT Pub. Date: Jul. 23, 2020

(65) Prior Publication Data
US 2023/0150914 A1     May 18, 2023

(30) Foreign Application Priority Data
Jan. 17, 2019  (WO) ................. PCT/EP2019/051120

(51) Int. Cl.
*C07C 69/675* (2006.01)
*C07C 67/08* (2006.01)
*C12P 7/62* (2022.01)

(52) U.S. Cl.
CPC ............ *C07C 69/675* (2013.01); *C07C 67/08* (2013.01); *C12P 7/62* (2013.01)

(58) Field of Classification Search
CPC .............................. C07C 69/675; C07C 67/08
See application file for complete search history.

(56) References Cited

U.S. PATENT DOCUMENTS

| 3,980,697 | A | * | 9/1976 | El-Chahawi | C07C 69/708 560/114 |
| 5,693,850 | A | * | 12/1997 | Birkhahn | A61K 31/22 560/189 |
| 2018/0303821 | A1 | * | 10/2018 | Sonner | A61K 31/4245 |

FOREIGN PATENT DOCUMENTS

| WO | 2013150153 | 10/2013 | | |
| WO | WO2013/150153 A1 | * | 10/2013 | ........... A61K 31/215 |
| WO | 2017147220 | 8/2017 | | |
| WO | WO2017147220 A1 | * | 8/2017 | ............. C07C 69/40 |

* cited by examiner

*Primary Examiner* — Yate' K Cutliff
(74) *Attorney, Agent, or Firm* — Edward E. Sowers; Brannon Sowers & Cracraft PC

(57) ABSTRACT

The invention relates to a method for producing lipids comprising structural units based on glycerides of 3-hydroxybutyric and/or 3-alkoxybutyric acids as well as the products thus obtained and their use.

5 Claims, No Drawings

METHOD FOR PRODUCING LIPIDS COMPRISING STRUCTURAL UNITS BASED ON GLYCERIDES OF HYDROXYCARBOXYLC ACIDS

CROSS-REFERENCES TO RELATED APPLICATIONS

This application is a National Stage filing of International Application PCT/EP 2019/051541 filed Jan. 23, 2019, entitled "METHOD FOR PRODUCING LIPIDS CONTAINING STRUCTURAL UNITS ON THE BASIS OF GLYCERIDES OF HYDROXY CARBOXYLIC ACIDS", claiming priority to PCT/EP 2019/051120, filed Jan. 17, 2019. The subject application claims priority to PCT/EP 2019/051541 and PCT/EP 2019/051120, and incorporates all by reference herein, in their entirety.

BACKGROUND OF THE INVENTION

The present invention relates to the field of keto bodies and related metabolism and the therapy of related diseases.

Especially, the present invention relates to a method for producing lipids comprising structural units based on glycerides of 3-hydroxybutyric and/or 3-alkoxybutyric acids as well as the reaction products thus obtainable or thus prepared (i.e. lipids comprising structural units based on glycerides of 3-hydroxybutyric and/or 3-alkoxybutyric acids) and their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i.e. lipids comprising structural units based on glycerides of 3-hydroxybutyric and/or 3-alkoxybutyric acids) obtainable or produced according to the inventive method, as well as their applications or uses.

Moreover, the present invention relates to food and/or food products, especially food supplements, functional foods, novel foods, food additives, food supplements, dietary foods, power snacks, appetite suppressants and strength and/or endurance sports supplements, which comprise the reaction products (i.e. lipids comprising structural units based on glycerides of 3-hydroxybutyric and/or 3-alkoxybutyric acids) obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetacetate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate), the latter being the most important of the three aforementioned compounds. 3-Hydroxybutyric acid or its salt occurs physiologically as the (R)-enantiomer, i.e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose al-most completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid.

| Indication | Therapeutic effect |
| --- | --- |
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e.g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts, especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i.e. synonymously also called beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that lipids comprising structural units based on glycerides of 3-hydroxybutyric and/or 3-alkoxybutyric acids represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing lipids comprising structural units based on glycerides of 3-hydroxybutyric and/or 3-alkoxybutyric acids.

Furthermore, the present invention relates—according to a second aspect of the present invention—to a reaction product obtainable according to the inventive method or a lipid comprising structural units based on glycerides of 3-hydroxybutyric and/or 3-alkoxybutyric acids or a mixture of at least two, especially at least three, lipids comprising structural units based on glycerides of 3-hydroxybutyric and/or 3-alkoxybutyric acids.

Likewise, the present invention—according to a third aspect of the present invention—relates to a pharmaceutical composition, especially a drug or medicament.

Furthermore, the present invention—according to a fourth aspect of the present invention—relates to an inventive reaction product or an inventive lipid comprising structural units based on glycerides of 3-hydroxybutyric and/or 3-alkoxybutyric acids or an inventive mixture of at least two, especially at least three, different lipids comprising structural units based on glycerides of 3-hydroxybutyric and/or 3-alkoxybutyric acids for the prophylactic and/or therapeutic treatment or for use in the prophylactic and/or therapeutic treatment of diseases of the human or animal body.

Furthermore, the present invention—according to a fifth aspect of the present invention—relates to the use of an inventive reaction product or an inventive lipid comprising structural units based on glycerides of 3-hydroxybutyric and/or 3-alkoxybutyric acids or an inventive mixture of at least two, especially at least three, different lipids comprising structural units based on glycerides of 3-hydroxybutyric and/or 3-alkoxybutyric acids for the prophylactic and/or therapeutic treatment or for producing a medicament for the prophylactic and/or therapeutic treatment of diseases of the human or animal.

Furthermore, the present invention—according to a sixth aspect of the present invention—relates to the use of an inventive reaction product or an inventive lipid comprising structural units based on glycerides of 3-hydroxybutyric and/or 3-alkoxybutyric acids or an inventive mixture of at least two, especially at least three, different lipids comprising structural units based on glycerides of 3-hydroxybutyric and/or 3-alkoxybutyric acids.

Furthermore, the present invention—according to a seventh aspect of the present invention—relates to a food and/or food product; further, especially special and/or advantageous embodiments of the food and/or food product.

Finally, the present invention—according to an eighth aspect of the present invention—relates to the use of a an inventive reaction product or an inventive lipid comprising structural units based on glycerides of 3-hydroxybutyric and/or 3-alkoxybutyric acids or an inventive mixture of at least two, especially at least three, different lipids comprising structural units based on glycerides of 3-hydroxybutyric and/or 3-alkoxybutyric acids in a food and/or a food product.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art. in addition, the skilled person may, if necessary, deviate from the following range specifications without leaving the scope of the present invention.

In addition, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject-matter of the present invention—according to a first aspect of the present invention—is thus a method for producing lipids comprising structural units based on glycerides of 3-hydroxybutyric and/or 3-alkoxybutyric acids, wherein at least one glyceride of the general formula (I)

$$R^1O-CH_2-CH(OR^2)-CH_2-OR^3 \quad (I)$$

wherein in the general formula (I) the radicals $R^1$, $R^2$ and $R^3$, identical or different, each independently of one another represent
hydrogen,
a radical $C_1$-$C_{11}$-alkyl-C(O)—, especially $C_2$-$C_{11}$-alkyl-C(O)—,
a radical $C_{12}$-$C_{29}$-alkyl-C(O)—, especially $C_{19}$-$C_{29}$-alkyl-C(O)—,
however, with the proviso that at least one, preferentially at least two, of the radicals $R^1$, $R^2$ and $R^3$ do not represent hydrogen,
is reacted
with at least one 3-hydroxybutyric and/or 3-alkoxybutyric acid derivative of the general formula (II)

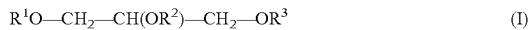

$$CH_3-CH(OR^4)-CH_2-C(O)OR^5 \quad (II)$$

wherein in the general formula (II)
the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—,
the radical $R^5$ represents hydrogen or $C_1$-$C_4$-alkyl, especially $C_1$-$C_4$-alkyl, preferably methyl or ethyl, more preferably ethyl, so that, as a reaction product, there is/are obtained one or more lipids comprising structural units based on glycerides of 3-hydroxybutyric and/or 3-alkoxybutyric acids of the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent
a radical $C_1$-$C_{11}$-alkyl-C(O)—, especially $C_2$-$C_{11}$-alkyl-C(O)—,
a radical $C_{12}$-$C_{29}$-alkyl-C(O)—, especially $C_{19}$-$C_{29}$-alkyl-C(O)—,
a radical $CH_3$—CH(OR^4)—$CH_2$—C(O)—, wherein the radical $R^4$ has the meaning defined hereinabove,
however, with the proviso that at least one of the radicals $R^6$, $R^7$ and $R^8$ represents a radical $CH_3$—CH(OR^4)—$CH_2$—C(O)—.

As stated above, the applicant has, quite surprisingly, discovered that the lipids comprising structural units based on glycerides of 3-hydroxybutyric and/or 3-alkoxybutyric acids thus produced are efficient, since physiologically compatible precursors and/or metabolites of free 3-hydroxybutyric acid or their salts, which can also be used in larger quantities in pharmaceutical or clinical applications because they are physiologically compatible.

The above-mentioned lipids comprising structural units based on glycerides of 3-hydroxybutyric and/or 3-alkoxybutyric acids, which are accessible for the first time in an efficient manner through the production method according to the invention, represent a physiologically and pharmacologically relevant alternative to free 3-hydroxybutyric acid or its salts.

The production of such compounds by means of conventional organic synthesis is complex and costly, since 3-hydroxybutyric acid has an increased tendency to polymerize and to undergo other undesirable side reactions (e. g. dehydration, decomposition, etc.). Within the scope of the present invention, it was possible for the first time to provide an efficiently working production method with which lipids comprising structural units based on glycerides of 3-hydroxybutyric and/or 3-alkoxybutyric acids can be produced without undesired side reactions, especially in a single step.

The inventive method thus makes it possible for the first time to provide non-toxic lipids comprising structural units based on glycerides of 3-hydroxybutyric and/or 3-alkoxybutyric acids from known, commercially available and above all physiologically harmless components or educts (starting compounds). The resulting lipids comprising structural units based on glycerides of 3-hydroxybutyric and/or 3-alkoxybutyric acids can be broken down physiologically, especially in the stomach and/or bowel, and release or generate the target molecule "3-hydroxybutyric acid" or its salts as active ingredient or active component.

In addition, the aforementioned lipids comprising structural units based on glycerides of 3-hydroxybutyric and/or 3-alkoxybutyric acids also comprise an acceptable taste to ensure compatibility even when administered orally in larger quantities over a longer period of time (e. g. administration of 50 g daily dose or more).

Similarly, the production method according to the invention makes it possible to provide the lipids comprising structural units based on glycerides of 3-hydroxybutyric and/or 3-alkoxybutyric acids free from toxic impurities.

In addition, with appropriate starting materials, the method can also be carried out enantioselectively. For example, according to the invention, the production method

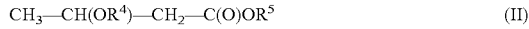

allows the biologically relevant form, i.e. the (R)-enantiomer, to be enriched, especially by enzyme catalysis, as not to burden the renal system of patients when administered orally (i.e. elimination via the kidneys). In principle, however, it is also possible, and under certain conditions may be useful, to enrich the (S)-enantiomer.

In addition, the production method according to the invention, including optional further processing or purification steps, can be operated economically and can also be implemented on a large scale.

Especially, the inventive production method uses commercially available starting compounds and furthermore allows a relatively simple process management even in case of large-scale implementation.

In contrast to conventional prior art production methods, the production method according to the invention does not use such complex starting materials and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

As far as the starting compounds or educt of the general formula (I) are concerned, the following should be mentioned:

According to a particular embodiment of the inventive method, it may be provided that in the general formula (I) the radicals $R^1$, $R^2$ and $R^3$, identical or different, each independently of one another represent hydrogen, a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—, however, with the proviso that at least one, preferentially at least two, of the radicals $R^1$, $R^2$ and $R^3$ do not represent hydrogen.

According to another particular embodiment of the inventive method, it may be provided that in the general formula (I) the radicals $R^1$, $R^2$ and $R^3$, identical or different, each independently of one another represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—.

According to yet another particular embodiment of the inventive method, it may be provided that in the general formula (I) the radicals $R^1$, $R^2$ and $R^3$, identical or different, each independently of one another represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—, however, with the proviso that at least one of the radicals $R^1$, $R^2$ and $R^3$ represents a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—.

According to yet a further particular embodiment of the inventive method, it may be provided that in the general formula (I) the radicals $R^1$, $R^2$ and $R^3$, identical or different, each independently of one another represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—, however, with the proviso that at least one of the radicals $R^1$, $R^2$ and $R^3$ represents a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—.

Finally, according to yet another further particular embodiment of the inventive method, it may be provided that identical or different, in the general formula (I) the radicals $R^1$, $R^2$ and $R^3$, identical or different, each independently of one another represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—, however, with the proviso that at least one of the radicals $R^1$, $R^2$ and $R^3$ represents a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, and with the proviso that at least one of the radicals $R^1$, $R^2$ and $R^3$ represents a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—.

Especially, it may be provided that in the general formula (I) the radicals $R^1$, $R^2$ and $R^3$, identical or different, each independently of one another represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—.

Furthermore, it may also be provided that in the general formula (I) the radicals $R^1$, $R^2$ and $R^3$, identical or different, each independently of one another represent a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—.

As far as the starting compounds or educt of the general formula (II) are concerned, the following should be mentioned:

In accordance with a particular embodiment of the method according to the invention, it may be provided that in the general formula (II)

the radical $R^4$ represents hydrogen or a radical of the type linear (straight-chain) or branched, saturated or mono- or polyunsaturated $C_1$-$C_{30}$-alkyl-C(O)—, especially linear (straight-chain) or branched, saturated or mono- or polyunsaturated $C_1$-$C_{21}$-alkyl-C(O)—, preferentially linear (straight-chain) or branched, saturated or mono- or polyunsaturated $C_3$-$C_{21}$-alkyl-C(O)—, the radical $R^5$ represents $C_1$-$C_4$-alkyl, especially $C_1$-$C_4$-alkyl, preferably methyl or ethyl, more preferably ethyl.

In accordance with another particular embodiment of the method according to the invention, it may be provided that in the general formula (II)

the radical $R^4$ represents hydrogen or a radical of the type linear (straight-chain) or branched, saturated or mono- or polyunsaturated $C_1$-$C_{30}$-alkyl-C(O)—, especially linear (straight-chain) or branched, saturated or mono- or polyunsaturated $C_1$-$C_{21}$-alkyl-C(O)—, preferentially linear (straight-chain) or branched, saturated or mono- or polyunsaturated $C_3$-$C_{21}$-alkyl-C(O)—, the radical $R^5$ represents ethyl.

In accordance with a further particular embodiment of the invention, it may be provided that in the general formula (II) the radical $R^4$ represents hydrogen and the radical $R^5$ represents ethyl.

Especially, as a 3-hydroxy- and/or 3-alkoxybutyric acid derivative of the general formula (II), 3-hydroxybutyric acid ethyl ester (ethyl 3-hydroxybutyrate) of the formula $CH_3$—CH(OH)—$CH_2$—C(O)O$C_2H_5$ may be used.

In principle, the 3-hydroxybutyric and/or 3-alkoxybutyric acid derivative of the general formula (II) may be used in racemic form or in the form of the (R)-enantiomer. The (R)-configuration is especially based on the carbon atom in 3-position or the (R)-configuration is based on the carbon atom carrying the $OR^4$ radical.

Especially, in the inventive method, the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

Especially, according to the invention, it may be provided that the reaction is carried out in the presence of a catalyst, especially an enzyme and/or a metal-containing and/or metal-based, acidic or basic catalyst, preferentially in the presence of an enzyme. Especially, the catalyst may be recycled after the reaction.

According to a particular embodiment of the inventive method, the reaction may be carried out in the presence of an enzyme as a catalyst.

Especially, the enzyme may be selected from synthetases (ligases), catalases, esterases, lipases and combinations thereof.

Especially, the enzyme may be derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially of *Candida antarctica, Mucor miehei (Rhizomucor miehei)* and *Thermomyces lanuginosus*.

Especially, the enzyme may be used in immobilized form, especially immobilized on a carrier, preferentially on a polymeric carrier, preferably on a polymeric organic carrier, more preferably with hydrophobic properties, even more preferably on a poly(meth)acrylic resin-based carrier.

Especially, the enzyme may be recycled after the reaction.

If the reaction is carried out in the presence of an enzyme as a catalyst, the reaction in the presence of an enzyme as a catalyst may especially be carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

The enzyme may especially be used in amounts, based on the total amount of starting compounds (I) and (II), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight.

The reaction in the presence of an enzyme as a catalyst may especially be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative particular embodiment of the inventive method, the reaction may be carried out in the presence of a metal-containing and/or metal-based, acidic or basic catalyst.

Especially, the catalyst may be selected from (i) basic catalysts, especially alkali or alkaline earth hydroxides and alkali or alkaline earth alcoholates, such as NaOH, KOH, LiOH, Ca(OH)$_2$, NaOMe, KOMe and Na(OBu-tert), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

Especially, an alkali or alkaline earth alcoholate may be used as a catalyst.

Especially, it is preferred if the catalyst is recycled after the reaction.

According to the invention, the reaction may especially be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

The catalyst may especially be used in amounts, based on the total amount of starting compounds (I) and (II), in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight.

The reaction in the presence of a metal-containing and/or metal-based, acidic or basic catalyst may especially be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

With regard to the production of the starting compounds or educts, the following should be mentioned:

in the case that in the general formula (I) at least one of the radicals $R^1$, $R^2$ and $R^3$ represents a radical $C_1$-$C_{11}$-alkyl-C(O)—, especially $C_2$-$C_{11}$-alkyl-C(O)—, and at least one of the radicals $R^1$, $R^2$ and $R^3$ represents a radical $C_{12}$-$C_{29}$-alkyl-C(O)—, especially $C_{19}$-$C_{29}$-alkyl-C(O)—, the glyceride of the general formula (I) is obtainable by appropriate transesterification or the glyceride of the general formula (I) may be obtained by appropriate transesterification.

According to a particular embodiment of the inventive method, the transesterification may be carried out by reacting, under transesterification conditions, at least one compound of the general formula (Ia)

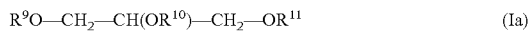  (Ia)

wherein in the general formula (Ia) the radicals $R^9$, $R^{10}$ and $R^{11}$, identical or different, each independently of one another represent
hydrogen,
a radical $C_1$-$C_{11}$-alkyl-C(O)—, especially $C_2$-$C_{11}$-alkyl-C(O)—,
however, with the proviso that at least two and preferentially the radicals $R^9$, $R^{10}$ and $R^{11}$ do not represent hydrogen, with at least one compound of general formula (Ib)

  (Ib)

wherein in the general formula (Ib) the radicals $R^{12}$, $R^{13}$ and $R^{14}$, identical or different, each independently of one another represent
hydrogen,
a radical $C_{12}$-$C_{29}$-alkyl-C(O)—, especially $C_{19}$-$C_{29}$-alkyl-C(O)—,
however, with the proviso that at least two and preferentially the radicals $R^{12}$, $R^{13}$ and $R^{14}$ do not represent hydrogen, or (vice versa)

at least one compound of the general formula (Ib), as defined hereinabove, is reacted under transesterification conditions with at least one compound of the general formula (Ia), as defined hereinabove.

In the general formula (Ia) the radicals $R^9$, $R^{10}$ and RD, identical or different, each independently of one another may especially represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—.

Furthermore, in the general formula (Ib) the radicals $R^{12}$, $R^{13}$ and $R^{14}$, identical or different, each independently of one another may especially represent a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—.

Especially, it may be provided according to the invention that, in the case that in the general formula (Ia) one of the radicals $R^9$, $R^{10}$ and $R^{11}$ represents hydrogen, the compound of the general formula (Ia) is obtainable and/or is obtained by partial hydrolysis, especially partial (selective) enzymatically catalyzed hydrolysis of a respective starting triglyceride of the general formula (Ia), wherein none of the radicals $R^9$, $R^{10}$ and $R^{11}$ represents hydrogen and/or wherein radicals $R^9$, $R^{10}$ and $R^{11}$, identical or different, each independently of one another represent a radical $C_1$-$C_{11}$-alkyl-C(O)—, especially $C_2$-$C_{11}$-alkyl-C(O)—.

Furthermore, according to the invention, it may especially be provided that in the case that in the general formula (Ib) one of the radicals $R^{12}$, $R^{13}$ and $R^{14}$ represents hydrogen, the compound of the general formula (Ib) is obtainable and/or is obtained by partial hydrolysis, especially partial (selective) enzymatically catalyzed hydrolysis of a respective starting triglyceride of the general formula (Ib), wherein none of the radicals $R^{12}$, $R^{13}$ and $R^{14}$ represents hydrogen and/or wherein radicals $R^{12}$, $R^{13}$ and $R^{14}$, identical or different, each independently of one another represent a radical $C_{12}$-$C_{29}$-alkyl-C(O)—, especially $C_{19}$-$C_{29}$-alkyl-C(O)—.

In accordance with a particular embodiment of the inventive method, it may be intended that the transesterification is carried out enzyme catalytically.

According to this particular embodiment of the inventive method, according to which the transesterification is carried out in the presence of an enzyme as a catalyst, the enzyme may be selected from synthetases (ligases), catalases, esterases, lipases and combinations thereof. Especially, the enzyme may be derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially of *Candida antarctica, Mucor miehei (Rhizomucor miehei)* and *Thermomyces lanuginosus*. Especially, the enzyme may be used in immobilized form, especially immobilized on a carrier, preferentially on a polymeric carrier, preferably on a polymeric organic carrier, more preferably with hydrophobic properties, even more preferably on a poly(meth)acrylic resin-based carrier. Preferably, the enzyme may be recycled after the transesterification.

Especially, the transesterification may be carried out in the presence of an enzyme as a catalyst at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

Especially, the enzyme may be used in amounts, based on the total amount of starting compounds (Ia) and (Ib), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight.

The transesterification may be carried out in the presence of an enzyme as a catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

In accordance with a particular embodiment of the inventive method, it may be provided that, in the case that in the general formula (II) the radical $R^4$ is a radical $C_1$-$C_{30}$-alkyl-C(O)—, especially $C_1$-$C_{21}$-alkyl-C(O)—, preferentially $C_3$-$C_{21}$-alkyl-C(O)—, the 3-hydroxybutyric and/or 3-alkoxybutyric acid derivative of the general formula (II) is obtainable and/or is obtained by reacting a compound of the general formula (IV)

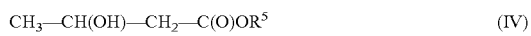
CH$_3$—CH(OH)—CH$_2$—C(O)OR$^5$ (IV)

wherein in the general formula (IV) the radical $R^5$ has the meaning defined hereinabove, especially represents hydrogen or $C_1$-$C_4$-alkyl, especially $C_1$-$C_4$-alkyl, preferably methyl or ethyl, more preferably ethyl, with at least one carboxylic acid anhydride of the general formula (V)

R$^{15}$—C(O)—O—C(O)—R$^{16}$ (V)

wherein in the general formula (V) the radicals $R^{15}$ and $R^{16}$, identical or different, each independently of one another represent a radical $C_1$-$C_{30}$-alkyl-C(O)—, especially $C_1$-$C_{21}$-alkyl-C(O)—, preferentially $C_3$-$C_{21}$-alkyl-C(O)—, optionally followed by hydrolysis in the case that $R^5$ represents hydrogen.

Especially, the reaction of the at least one compound of the general formula (IV) with the at least one carboxylic anhydride of the general formula (V) may be carried out at temperatures in the range of from 60 to 150° C., especially in the range of from 70 to 120° C., preferentially in the range of from 80 to 100° C.

Furthermore, the reaction of the at least one compound of the general formula (IV) with the at least one carboxylic acid anhydride of the general formula (V) may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, very particularly at about 1 bar.

Especially, during the reaction of the at least one compound of the general formula (IV) with the one with at least one carboxylic acid anhydride of the general formula (V), a compound of the general formula (VI)

R$^{17}$—C(O)—OH (VI)

is formed simultaneously, wherein the radical $R^{17}$ represents a radical $R^{15}$ or $R^{16}$ each with meaning defined hereinabove. Especially, the compound according to the general formula (VI) may be withdrawn during or after the reaction has taken place, especially after the reaction has taken place, preferably by distillation.

According to a particular embodiment, it may be provided that, in the case that in the general formula (V) the radicals $R^{15}$ and $R^{16}$ differ from one another, and/or in the case that in the general formula (V) the radicals $R^{15}$ and $R^{16}$ each represent an alkyl radical having more than two carbon atoms, the carboxylic anhydride of the general formula (V) is obtainable and/or is obtained by reacting acetic anhydride (acetic anhydride) with at least one carboxylic acid of the general formula (VII)

R$^{18}$—C(O)—OH (VII)

wherein the radical $R^{18}$ represents a radical $R^{15}$ or $R^{16}$ each with the meaning defined hereinabove, however, with the proviso that the radicals $R^5$ and $R^{16}$ are different from one another and/or that the radicals $R^{15}$ and $R^{16}$, identical or different, each independently of one another represent an alkyl radical having more than two carbon atoms.

Especially, the reaction of acetic anhydride with the at least one carboxylic acid of the general formula (VII) takes place according to the reaction equation

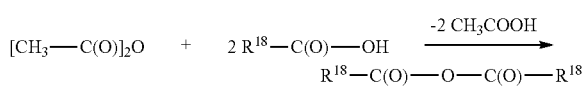
[CH$_3$—C(O)]$_2$O + 2 R$^{18}$—C(O)—OH $\xrightarrow{-2\ CH_3COOH}$ R$^{18}$—C(O)—O—C(O)—R$^{18}$ The reaction of acetic anhydride with the at least one carboxylic acid of the general formula (VII) may be carried out at temperatures in the range of from 60 to 150° C., especially in the range of from 70 to 120° C., preferentially in the range of from 80 to 100° C.

The reaction of acetic anhydride with the at least one carboxylic acid of the general formula (VII) may be carried out at a pressure in the range of from 0.0001 bar to 10 bar, especially in the range of from 0.001 bar to 5 bar, preferentially in the range of from 0.01 bar to 2 bar, more preferably in the range from 0.05 bar to 1 bar, more particularly at about 1 bar.

In accordance with this synthesis, especially a symmetrical carboxylic acid anhydride of the general formula (V) may be produced. Especially, in the general formula (V) the radicals $R^{15}$ and $R^{16}$ are identical and represent an alkyl group having more than two carbon atoms.

According to an alternative embodiment, however, an asymmetric carboxylic acid anhydride of the general formula (V) may also be produced in accordance with this synthesis. Especially, in the general formula (V) the radicals $R^{15}$ and $R^{16}$ may be different from one another. Preferentially, in the general formula (V) the radicals $R^{15}$ and $R^{16}$ each represent an alkyl radical having more than two carbon atoms.

In the context of inventive production method, in the case that in general formula (II) the radical $R^5$ denotes hydrogen, its anhydride of the general formula (IIa)

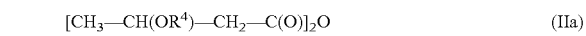
[CH$_3$—CH(OR$^4$)—CH$_2$—C(O)]$_2$O (IIa)

wherein in the general formula (IIa) the radical $R^4$ has the meaning defined hereinabove, may be used instead of the free acid.

In the context of the inventive production method, as a reaction product, one or more lipids comprising structural units based on glycerides of 3-hydroxybutyric and/or 3-alkoxybutyric acids and corresponding to the general formula (III)

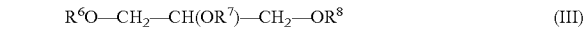
R$^6$O—CH$_2$—CH(OR$^7$)—CH$_2$—OR$^8$ (III)

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $C_{12}$-$C_{29}$-alkyl-C(O)—, especially $C_{19}$-$C_{29}$-alkyl-C(O)—, a radical CH$_3$— CH(OR$^4$)—CH$_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that at least one of the radicals $R^6$, $R^7$ and $R^8$ represents a radical $CH_3$—$CH(OR^4)$—$CH_2$—$C(O)$—, is/are obtained.

Especially, in the context of the inventive production method, as a reaction product, one or more lipids comprising structural units based on glycerides of 3-hydroxybutyric and/or 3-alkoxybutyric acids and corresponding to the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent a radical of the type linear (straight-chain) or branched, saturated or mono- or polyunsaturated $C_1$-$C_{11}$-alkyl-$C(O)$—, especially linear (straight-chain) or branched, saturated or mono- or polyunsaturated $C_2$-$C_{11}$-alkyl-$C(O)$—, a radical of the type linear (straight-chain) or branched, saturated or mono- or polyunsaturated $C_{12}$-$C_{29}$-alkyl-$C(O)$—, especially linear (straight-chain) or branched, saturated or mono- or polyunsaturated $C_{19}$-$C_{29}$-alkyl-$C(O)$—, a radical of the type linear (straight-chain) or branched, saturated or mono- or polyunsaturated $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-$C(O)$—, especially $C_1$-$C_{21}$-alkyl-$C(O)$—, preferentially $C_3$-$C_{21}$-alkyl-$C(O)$—, however, with the proviso that at least one of the radicals $R^6$, $R^7$ and $R^0$ represents a radical $CH_3$—$CH(OR^4)$—$CH_2$—$C(O)$—.

may be obtained.

Especially, in the context of the inventive production method, as a reaction product, one or more lipids comprising structural units based on glycerides of 3-hydroxybutyric and/or 3-alkoxybutyric acids and corresponding to the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent a radical $C_1$-$C_{11}$-alkyl-$C(O)$—, especially $C_2$-$C_{11}$-alkyl-$C(O)$—, a radical $C_{12}$-$C_{29}$-alkyl-$C(O)$—, especially $C_{19}$-$C_{29}$-alkyl-$C(O)$—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-$C(O)$—, especially $C_1$-$C_{21}$-alkyl-$C(O)$—, preferentially $C_3$-$C_{21}$-alkyl-$C(O)$—, however, with the proviso that two radicals $R^6$, $R^7$ and $R^e$ represent a radical $CH_3$—$CH(OR^4)$—$CH_2$—$C(O)$—, may be obtained.

According to a particular embodiment of the inventive production method, as a reaction product, one or more lipids comprising structural units based on glycerides of 3-hydroxybutyric and/or 3-alkoxybutyric acids and corresponding to the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent a radical $C_1$-$C_{11}$-alkyl-$C(O)$—, especially $C_2$-$C_{11}$-alkyl-$C(O)$—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-$C(O)$—, especially $C_1$-$C_{21}$-alkyl-$C(O)$—, preferentially $C_3$-$C_{21}$-alkyl-$C(O)$—, however, with the proviso that two radicals $R^6$, $R^7$ and $R^8$ represent a radical $CH_3$—$CH(OR^4)$—$CH_2$—$C(O)$—, may be obtained.

According to another particular embodiment of the inventive production method, as a reaction product, one or more lipids comprising structural units based on glycerides of 3-hydroxybutyric and/or 3-alkoxybutyric acids and corresponding to the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent a radical $C_{12}$-$C_{29}$-alkyl-$C(O)$—, especially $C_{19}$-$C_{29}$-alkyl-$C(O)$—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-$C(O)$—, especially $C_1$-$C_{21}$-alkyl-$C(O)$—, preferentially $C_3$-$C_{21}$-alkyl-$C(O)$—, however, with the proviso that two radicals $R^6$, $R^7$ and $R^8$ represent a radical $CH_3$—$CH(OR^4)$—$CH_2$—$C(O)$—, may be obtained.

According to a further particular embodiment of the inventive production method, as a reaction product, one or more lipids comprising structural units based on glycerides of 3-hydroxybutyric and/or 3-alkoxybutyric acids and corresponding to the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent a radical $C_1$-$C_{11}$-alkyl-$C(O)$—, especially $C_2$-$C_{11}$-alkyl-$C(O)$—, a radical $C_{12}$-$C_{29}$-alkyl-$C(O)$—, especially $C_{19}$-$C_{29}$-alkyl-$C(O)$—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-$C(O)$—, especially $C_1$-$C_{21}$-alkyl-$C(O)$—, preferentially $C_3$-$C_{21}$-alkyl-$C(O)$—, however, with the proviso that one of the radicals $R^6$, $R^7$ and $R^8$ represents a radical $CH_3$—$CH(OR^4)$—$CH_2$—$C(O)$—, may be obtained.

According to yet another particular embodiment of the inventive production method, as a reaction product, one or more lipids comprising structural units based on glycerides of 3-hydroxybutyric and/or 3-alkoxybutyric acids and corresponding to the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $CH_3$—CH(OR$^4$)—$CH_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that one of the radicals $R^6$, $R^7$ and $R^8$ represents a radical $CH_3$—CH(OR$^4$)—$CH_2$—C(O)—, may be obtained.

Furthermore, according to another particular embodiment of the inventive production method, as a reaction product, one or more lipids comprising structural units based on glycerides of 3-hydroxybutyric and/or 3-alkoxybutyric acids and corresponding to the general formula (III)

$$R^6O—CH_2—CH(OR^7)—CH_2—OR^8 \quad (III)$$

wherein in the general formula (III) the radicals $R^6$, $R^7$ and $R^8$, identical or different, each independently of one another represent a radical $C_{12}$-$C_{29}$-alkyl-C(O)—, especially $C_{19}$-$C_{29}$-alkyl-C(O)—, a radical $CH_3$—CH(OR$^4$)—$CH_2$—C(O)—, wherein the radial $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that one of the radicals $R^6$, $R^7$ and $R^8$ represents a radical $CH_3$—CH(OR$^4$)—$CH_2$—C(O)—, may be obtained.

Finally, in accordance with a further particular embodiment of the inventive production method, as a reaction product, one or more lipids comprising structural units based on glycerides of 3-hydroxybutyric and/or 3-alkoxybutyric acids and corresponding to the general formula (III)

$$R^6O—CH_2—CH(OR^7)—CH_2—OR^8 \quad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $C_{12}$-$C_{29}$-alkyl-C(O)—, especially $C_{19}$-$C_{29}$-alkyl-C(O)—, a radical $CH_3$—CH(OR$^4$)—$CH_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that one of the radicals $R^6$, $R^7$ and $R^8$ represents a radical $CH_3$—CH(OR$^4$)—$CH_2$—C(O)— and that one of the radicals $R^6$, $R^7$ and $R^8$ represents a radical $C_1$-$C_{11}$-alkyl-C(O)—, especially $C_2$-$C_{11}$-alkyl-C(O)—, and that one of the radicals $R^6$, $R^7$ and $R^B$ represents a radical $C_{12}$-$C_{29}$-alkyl-C(O)—, especially $C_{19}$-$C_{29}$-alkyl-C(O)—, may be obtained.

As mentioned hereinbefore, the method according to the invention is usually carried out in the absence of solvents and/or without any solvent (i.e. as a reaction in mass or as a reaction in substance or as a so-called bulk reaction). This has the advantage that the reaction products obtained are not contaminated with solvent and no solvent has to be removed and disposed of or recycled in a costly and energy-intensive manner after the method or reaction has been carried out. Surprisingly, the method or reaction nevertheless proceeds with high conversions and yields and at least essentially without significant by-product formation.

The inventive method is illustrated, purely by way of example and in a nonlimiting way, by the following general reaction scheme. In this scheme, the radical $R^{1'}$ denotes a radical $C_{12}$-$C_{29}$-alkyl, the radical $R^{2'}$ denotes a radical $C_1$-$C_{11}$-alkyl and the radical $R^{3'}$ denotes hydrogen or a radical $C_1$-$C_{30}$-alkyl-C(O)—, especially $C_1$-$C_{21}$-alkyl-C(O)—, preferentially $C_3$-$C_{21}$-Alkyl-C(O)—. A radical $R^{2'}$-MCT-oil denotes a triglyceride with the radical $R^{2'}$. A radical $R^{1'}$-MCT-oil denotes a triglyceride with the radical $R^{1'}$. 3-Acetoxy-BHB anhydride is the anhydride of 3-acetoxybutyric acid. 3-$R^{3'}$-BHB-EE is the ethyl ester of 3-acetoxybutyric acid. The abbreviation "cat" stands for a catalyst (e.g. enzyme or chemical catalyst such as alcoholate etc.). As the following reaction scheme illustrates, different triglycerides of 3-BHB can be obtained with the inventive method, which can be further randomized, especially e.g. with medium and/or long-chain triglycerides or fatty acids, especially with so-called fish oils.

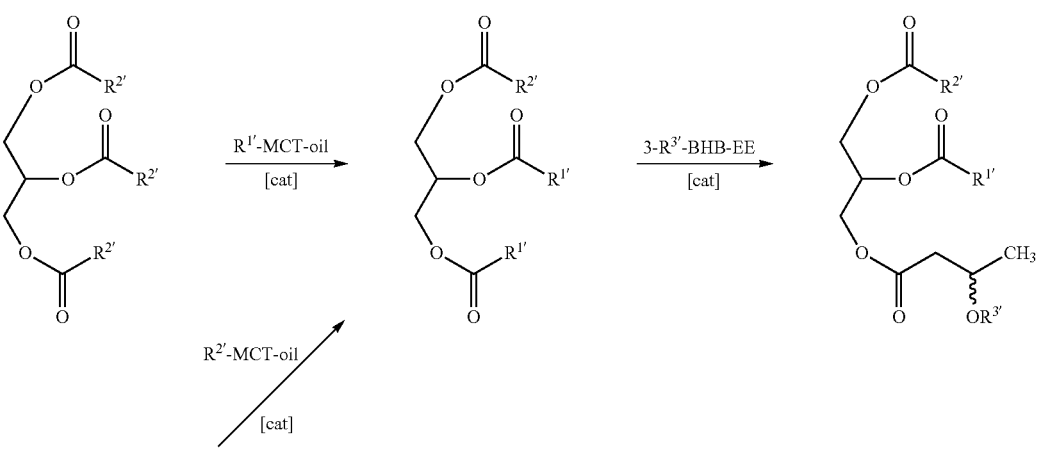

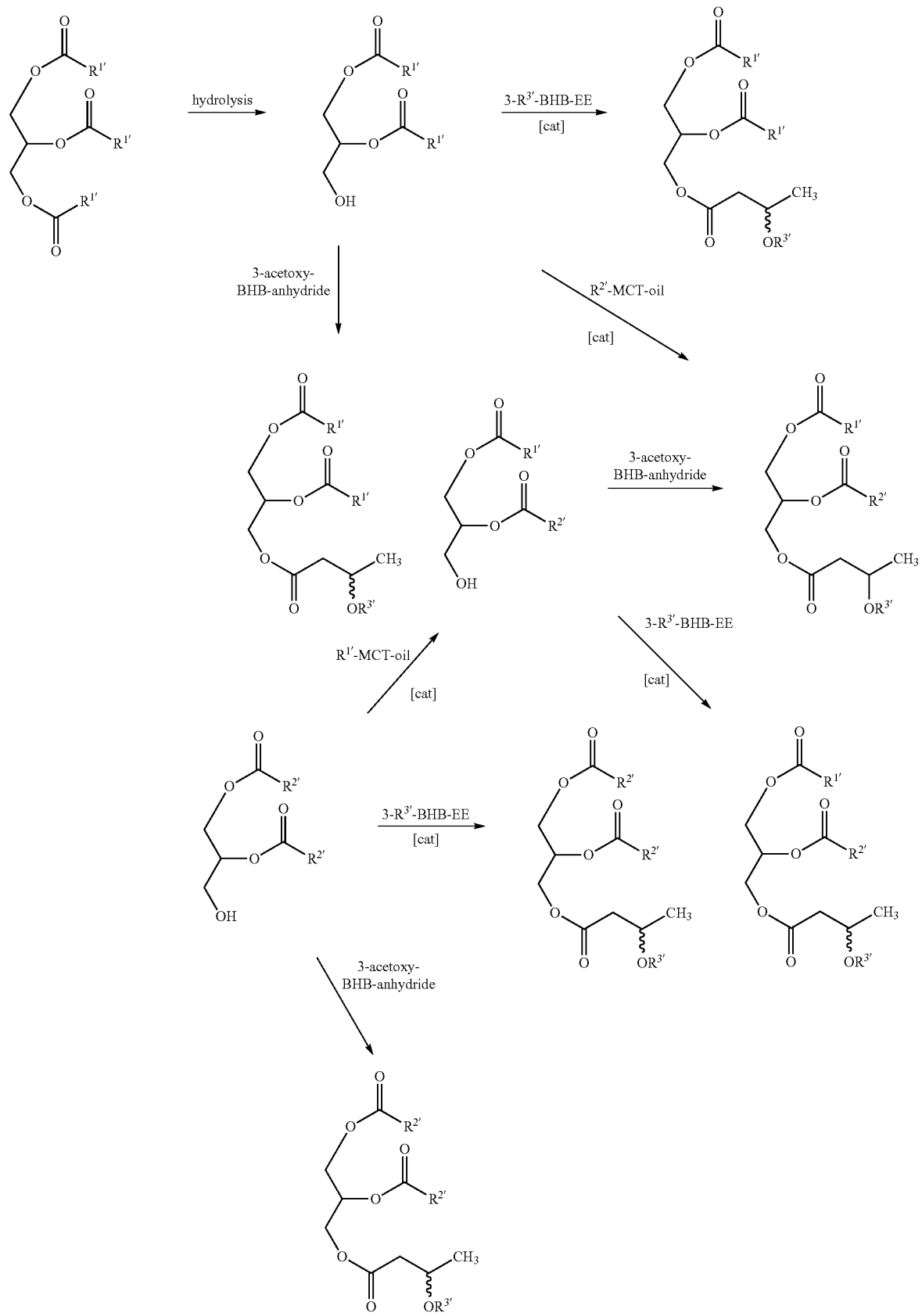

A further subject-matter—according to a second aspect of the present invention—is the reaction product obtainable according to the inventive method or the inventive reaction product (i. e. one or more lipids comprising structural units based on glycerides of 3-hydroxybutyric and/or 3-alkoxybutyric acids) (cf. claims 36 to 47).

Especially, the subject-matter of the present invention according to this aspect of the invention are lipids comprising structural units based on glycerides of 3-hydroxybutyric and/or 3-alkoxybutyric acids, as defined in claims 48 to 56.

Especially, the subject-matter of the present invention according to this aspect of the present invention is a lipid comprising structural units based on glycerides of 3-hydroxybutyric and/or 3-alkoxybutyric acids, wherein the lipid comprising structural units based on glycerides of 3-hydroxybutyric and/or 3-alkoxybutyric acids corresponds to the general formula (III)

$$R^6O\text{—}CH_2\text{—}CH(OR^7)\text{—}CH_2\text{—}OR^8 \qquad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $C_{12}$-$C_{29}$-alkyl-C(O)—, especially $C_{19}$-$C_{29}$-alkyl-C(O)—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that at least one of the radicals $R^6$, $R^7$ and $R^8$ represents a radical $CH_3$—$CH(OR^4)$—$CH_2$—$C(O)$— (and preferentially with the further proviso that in the case that all radicals $R^6$, $R^7$ and $R^8$ represent a radical $CH_3$—$CH(OR^4)$—$CH_2$—$C(O)$—, in at least one of the radicals $R^6$, $R^7$ and $R^8$ the radical $R^4$ present in the radical $CH_3$—$CH(OR^4)$—$CH_2$—$C(O)$— does not represent hydrogen).

Furthermore, the subject-matter of the present invention according to this aspect of the present invention is a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O\text{—}CH_2\text{—}CH(OR^7)\text{—}CH_2\text{—}OR^8 \qquad (III)$$

wherein in the general formula (III) the radicals $R^6$, $R^7$ and $R^8$, identical or different, each independently of one another represent a radical of the type linear (straight-chain) or branched, saturated or mono- or polyunsaturated $C_1$-$C_{11}$-alkyl-C(O)—, especially linear (straight-chain) or branched, saturated or mono- or polyunsaturated $C_2$-$C_{11}$-alkyl-C(O)—, a radical of the type linear (straight-chain) or branched, saturated or mono- or polyunsaturated $C_{12}$-$C_{29}$-alkyl-C(O)—, especially linear (straight-chain) or branched, saturated or mono- or polyunsaturated $C_{19}$-$C_{29}$-alkyl-C(O)—, a radical of the type linear (straight-chain) or branched, saturated or mono- or polyunsaturated $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that at least one of the radicals $R^6$, $R^7$ and $R^8$ represents a radical $CH_3$—$CH(OR^4)$—$CH_2$—$C(O)$—.

Again, a further subject-matter of the present invention according to this aspect of the invention is a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O\text{—}CH_2\text{—}CH(OR^7)\text{—}CH_2\text{—}OR^8 \qquad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $C_{12}$-$C_{29}$-alkyl-C(O)—, especially $C_{19}$-$C_{29}$-alkyl-C(O)—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that two radicals $R^6$, $R^7$ and $R^8$ represent a radical $CH_3$—$CH(OR^4)$—$CH_2$—$C(O)$—.

Another subject-matter of the present invention according to this aspect of the invention is a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O\text{—}CH_2\text{—}CH(OR^7)\text{—}CH_2\text{—}OR^8 \qquad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $CH_3$—$CH(OR^4)$—$CH_2$—$C(O)$—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that two radicals $R^6$, $R^7$ and $R^8$ represent a radical $CH_3$—$CH(OR^4)$—$CH_2$—$C(O)$—.

Furthermore, according to this aspect of the invention, the subject-matter of the present invention is also a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O\text{—}CH_2\text{—}CH(OR^7)\text{—}CH_2\text{—}OR^8 \qquad (III)$$

wherein in the general formula (III) the radicals $R^6$, $R^7$ and $R^8$, identical or different, each independently of one another represent a radical $C_{12}$-$C_{29}$-alkyl-C(O)—, especially $C_{19}$-$C_{29}$-alkyl-C(O)—, a radical $CH_3$—$CH(OR^4)$—$CH_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that two radicals $R^6$, $R^7$ and $R^8$ represent a radical $CH_3$—$CH(OR^4)$—$CH_2$—C(O)—.

A further subject-matter of the present invention according to this aspect of the invention is a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O—CH_2—CH(OR^7)—CH_2—OR^8 \quad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $C_{12}$-$C_{29}$-alkyl-C(O)—, especially $C_{19}$-$C_{29}$-alkyl-C(O)—, a radical $CH_3$—$CH(OR^4)$—$CH_2$—C(O)—, wherein the radical $R^4$ has the meaning defined hereinabove, especially wherein the radical $R^4$ represents hydrogen or a radical $C_1$-$C_3$-alkyl-C(O)—, especially $C_1$-$C_{21}$-alkyl-C(O)—, preferentially $C_3$-$C_{21}$-alkyl-C(O)—, however, with the proviso that one of the radicals $R^6$, $R^7$ and $R^8$ represents a radical $CH_3$—$CH(OR^4)$—$CH_2$—C(O)—.

Furthermore, according to this aspect of the invention, the present invention relates to a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O—CH_2—CH(OR^7)—CH_2—OR^8 \quad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $CH_3$— $CH(OR^4)$—$CH_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{22}$-alkyl-C(O)—, however, with the proviso that one of the radicals $R^6$, $R^7$ and $R^B$ represents a radical $CH_3$— $CH(OR^4)$—$CH_2$—C(O)—.

According to this aspect of the invention, the present invention also relates to a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O—CH_2—CH(OR^7)—CH_2—OR^8 \quad (III)$$

wherein in the general formula (III) the radicals $R^6$, $R^7$ and $R^8$, identical or different, each independently of one another represent a radical $C_{12}$-$C_{29}$-alkyl-C(O)—, especially $C_{19}$-$C_{29}$-alkyl-C(O)—, a radical $CH_3$—$CH(OR^4)$—$CH_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that one of the radicals $R^6$, $R^7$ and $R^8$ represents a radical $CH_3$— $CH(OR^4)$—$CH_2$—C(O)—.

Finally, according to this aspect of the invention, another subject-matter of the present invention is a lipid comprising structural units based on glycerides of 3-hydroxybutyric and/or 3-alkoxybutyric acids, especially as defined hereinabove, wherein the lipid comprising structural units based on glycerides of 3-hydroxybutyric and/or 3-alkoxybutyric acids corresponds to the general formula (III)

$$R^6O—CH_2—CH(OR^7)—CH_2—OR^8 \quad (III)$$

wherein in the general formula (III) the radicals $R^6$, $R^7$ and $R^8$, identical or different, each independently of one another represent a radical $C_1$-$C_{11}$-alkyl-C(O)—, especially $C_2$-$C_{11}$-alkyl-C(O)—, a radical $C_{12}$-$C_{29}$-alkyl-C(O)—, especially $C_{19}$-$C_{29}$-alkyl-C(O)—, a radical $CH_3$—$CH(OR^4)$—$CH_2$—C(O)—, wherein the radical $R^4$ has the meaning defined hereinabove, especially wherein the radical $R^4$ represents hydrogen or a radical $C_1$-$C_{30}$-alkyl-C(O)—, especially $C_1$-$C_{21}$-alkyl-C(O)—, preferentially $C_3$-$C_{21}$-alkyl-C(O)—, however, with the proviso that one of the radicals $R^6$, $R^7$ and $R^8$ represents a radical $CH_3$— $CH(OR^4)$—$CH_2$—C(O)— and that one of the radicals $R^6$, $R^7$ and $R^8$ represents a radical $C_1$-$C_{11}$-alkyl-C(O)—, especially $C_2$-$C_{11}$-alkyl-C(O)—, and that one of the radicals $R^6$, $R^7$ and $R^8$ represents a radical $C_{12}$-$C_{29}$-alkyl-C(O)—, especially $C_{19}$-$C_{29}$-alkyl-C(O)—.

A further subject-matter of the present invention according to this aspect of the invention is a mixture comprising at least two different lipids comprising structural units based on glycerides of 3-hydroxybutyric and/or 3-alkoxybutyric acids of the general formula (III), as defined hereinabove.

Especially, a further subject matter of the present invention according to this aspect of the invention is a mixture comprising at least three different lipids comprising structural units based on glycerides of 3-hydroxybutyric and/or 3-alkoxybutyric acids of the general formula (Ill), as defined hereinabove.

The reaction product obtainable according to the inventive method or the inventive reaction product as defined hereinabove, respectively, and/or the lipids comprising structural units based on glycerides of 3-hydroxybutyric and/or 3-alkoxybutyric acids obtainable according to the inventive method or the inventive lipids comprising structural units based on glycerides of 3-hydroxybutyric and/or 3-alkoxybutyric acids as defined hereinabove, respectively, and/or the mixture obtainable according to the inventive production method or the inventive mixture as defined hereinabove, respectively, comprises a multitude of advantages and special features compared to the prior art:

As the applicant has surprisingly found out, the reaction product obtainable according to the inventive method or the inventive reaction product as defined hereinabove, respectively, and/or the lipids comprising structural units based on glycerides of 3-hydroxybutyric and/or 3-alkoxybutyric acids obtainable according to the inventive production method or the inventive lipids comprising structural units based on glycerides of 3-hydroxybutyric and/or 3-alkoxybutyric acids as defined hereinabove, respectively, and/or the mixture obtainable according to the inventive production method or the inventive mixture as defined hereinabove, respectively, is especially suitable as a precursor or metabolite of 3-hydroxybutyric acid or its salts, since, on the one hand, it is converted physiologically, especially in the gastrointestinal tract, to 3-hydroxybutyric acid or its salts and, on the other hand, it simultaneously comprises a good physiological compatibility or tolerability, especially with regard to non-toxicity and acceptable organoleptic properties.

Moreover, the reaction product obtainable according to the inventive method or the inventive reaction product as defined hereinabove, respectively, and/or the lipids comprising structural units based on glycerides of 3-hydroxybutyric and/or 3-alkoxybutyric acids obtainable according to the inventive production method or the inventive lipids comprising structural units based on glycerides of 3-hydroxybutyric and/or 3-alkoxybutyric acids as defined hereinabove, respectively, and/or the mixture obtainable according to the inventive production method or the inventive mixture as defined hereinabove, respectively, is easily accessible or available on a large scale on a synthetic basis, even on a commercial scale, and with the required pharmaceutical or pharmacological quality.

Additionally, the reaction product obtainable according to the inventive method or the inventive reaction product as defined hereinabove, respectively, and/or the lipids comprising structural units based on glycerides of 3-hydroxybutyric and/or 3-alkoxybutyric acids obtainable according to the inventive production method or the inventive lipids comprising structural units based on glycerides of 3-hydroxybutyric and/or 3-alkoxybutyric acids as defined hereinabove, respectively, and/or the mixture obtainable according to the inventive production method or the inventive mixture as defined hereinabove, respectively, can, if necessary, be provided in enantiomerically pure or enantiomerically enriched form.

The reaction product obtainable according to the inventive method or the inventive reaction product as defined hereinabove, respectively, and/or the lipids comprising structural units based on glycerides of 3-hydroxybutyric and/or 3-alkoxybutyric acids obtainable according to the inventive production method or the inventive lipids comprising structural units based on glycerides of 3-hydroxybutyric and/or 3-alkoxybutyric acids as defined hereinabove, respectively, and/or the mixture obtainable according to the inventive production method or the inventive mixture as defined hereinabove, respectively, thus represents an efficient pharmacological drug target in the context of keto-body therapy of the human or animal body.

In the following, the remaining aspects of the invention are explained in more detail.

A further subject-matter of the present invention—according to a third aspect of the present invention—is a pharmaceutical composition, especially a drug or medicament, which comprises a reaction product obtainable according to the inventive production method or the inventive reaction product as defined hereinabove, respectively, and/or a lipid comprising structural units based on glycerides of 3-hydroxybutyric and/or 3-alkoxybutyric acids obtainable according to the inventive production method or the inventive a lipid comprising structural units based on glycerides of 3-hydroxybutyric and/or 3-alkoxybutyric acids as defined hereinabove, respectively, and/or a mixture obtainable according to the inventive production method or the inventive mixture as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject-matter of the present invention—according to a fourth aspect of the present invention—is a reaction product obtainable according to the inventive production method or the inventive reaction product as defined hereinabove, respectively, and/or a lipid comprising structural units based on glycerides of 3-hydroxybutyric and/or 3-alkoxybutyric acids obtainable according to the inventive production method or the inventive lipid comprising structural units based on glycerides of 3-hydroxybutyric and/or 3-alkoxybutyric acids as defined hereinabove, respectively, and/or a mixture obtainable according to the inventive production method or the inventive mixture as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a fifth aspect of the present invention—is the use of a reaction product obtainable according to the inventive production method or the inventive reaction product as defined hereinabove, respectively, and/or a lipid comprising structural units based on glycerides of 3-hydroxybutyric and/or 3-alkoxybutyric acids obtainable according to the inventive production method or the inventive lipid comprising structural units based on glycerides of 3-hydroxybutyric and/or 3-alkoxybutyric acids as defined hereinabove, respectively, and/or a mixture obtainable according to the inventive production method or the inventive mixture as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product obtainable according to the inventive production method or the inventive reaction product as defined hereinabove, respectively, and/or a lipid comprising structural units based on glycerides of 3-hydroxybutyric and/or 3-alkoxybutyric acids obtainable according to the inventive production method or the inventive lipid comprising structural units based on glycerides of 3-hydroxybutyric and/or 3-alkoxybutyric acids as defined hereinabove, respectively, and/or a mixture, obtainable according to the inventive production method or the inventive mixture as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a seventh aspect of the present invention—is a food and/or a food product, which comprises a reaction product obtainable according to the inventive production method or the inventive reaction product as defined hereinabove, respectively, and/or a lipid comprising structural units based on glycerides of 3-hydroxybutyric and/or 3-alkoxybutyric acids obtainable according to the inventive production method or the inventive lipid comprising structural units based on glycerides of 3-hydroxybutyric and/or 3-alkoxybutyric acids as defined hereinabove, respectively, and/or a mixture obtainable according to the inventive production method or the inventive mixture as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an eighth aspect of the present invention—is the use of a reaction product obtainable according to the inventive production method or the inventive reaction product as defined hereinabove, respectively, and/or a lipid comprising structural units based on glycerides of 3-hydroxybutyric and/or 3-alkoxybutyric acids obtainable according to the inventive production method or the inventive lipid comprising structural units based on glycerides of 3-hydroxybutyric and/or 3-alkoxybutyric acids as defined hereinabove, respectively, and/or a mixture obtainable according to the inventive production method or the inventive mixture as defined hereinabove, respectively, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and nonlimiting implementation and configuration of the present invention.

EXAMPLES

Examples of Production

The inventive production method is illustrated by the following examples. The relevant general reaction schemes are shown and explained in the general description section.

Example 1

Production of Mixed Triglycerides with Chains Based on Long Chain Fatty Acid (LCFA), Medium Chain Fatty Acid (MCFA) and 3-Hydroxybutyric Acid (BHB or 3-BHB) (i.e. Mixed Long Chain Fatty Acid (LCFA). Medium Chain Fatty Acid (MCFA) and 3-Hydroxybutyric Acid (3-BHB) Triglycerides)

In a 2,000-ml-multi-neck flask with dephlegmator (partial condenser) and distillation bridge, 500 g of a medium-chain triglyceride ($C_8/C_{10}$ fatty acid comprising triglyceride, ratio 60%/40%) and 900 g of a long-chain refined, bleached and deodorized fish oil (EPA/DHA content 20 to 50%, ratio 50:50) are reacted under stirring at 50 to 70° C. and under vacuum (<100 mbar) for 12 to 24 h using 14 g immobilized enzyme (CALB). The enzyme is then filtered out. The reaction product is a randomized LCF/MCF triglyceride.

In a 2,000-ml-multi-neck flask with dephlegmator (partial condenser) and distillation bridge, 1,000 g of the randomized LCF/MCF triglyceride prepared above are transesterified with 500 g (R)/(S)-3-hydroxybutyric acid ethyl ester (3-BHB ethyl ester) and 15 g immobilized enzyme (CALB, e.g. immobilized enzyme, e.g. CALB lipase on polymer carrier, derived from *Candida antarctica*, e.g. Novozym® 435 from Sigma-Aldrich or Merck or Lipozym® 435 from Strem Chemicals, Inc.) at 50 to 70° C. and under vacuum (<500 mbar) for 24 to 36 h. The enzyme is then filtered out.

The reaction product is a LCF/MCF/3-BHB triglyceride or a structured lipid.

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 2

Production of Mixed Triglycerides with Chains Based on Long Chain Fatty Acid (LCFA) and 3-Hydroxybutyric Acid (BHB or 3-BHB) (i.e. Mixed Long Chain Fatty Acid (LCFA) and 3-Hydroxybutyric Acid (3-BHB) Triglycerides)

In a 1,000-ml-multi-neck flask with dephlegmator (partial condenser) and distillation bridge, 500 g of a long-chain, refined, bleached and deodorized fish oil (EPA/DHA content 20 to 50%, ratio 50:50) are transesterified with 200 g (R)/(S)-3-hydroxybutyric acid ethyl ester (3-BHB ethyl ester) and 15 g immobilized enzyme (CALB) at 50 to 70° C. and under vacuum (<500 mbar) for 24 to 36 h. The enzyme is then filtered out.

The reaction product is a LCF/3-BHB triglyceride or a structured lipid.

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 3

Preparation of Mixed Medium Chain Fatty Acid (MCFA)/3-Hydroxybutyric Acid (3-BHB) Triglycerides In a 1,000-ml-multi-neck flask with dephlegmator (partial condenser) and distillation bridge, 500 g medium-chain triglyceride (triglyceride containing $C_8/C_{10}$ fatty acid, ratio 60%/40%) are transesterified with 120 g (R)/(S)-3-hydroxybutyric acid ethyl ester (3-BHB ethyl ester) and 15 g immobilized enzyme (CALB) at 50 to 70° C. and under vacuum (<500 mbar) for 24 to 36 h. The enzyme is then filtered out.

The reaction product is a MCF/3-BHB triglyceride or a structured lipid.

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 4

Preparation of Mixed Medium Chain Fatty Acid (MCFA) and 3-Acetoxybutyric Acid (Ac-BHB) Triglycerides from Partial Glycerides and 3-Acetoxybutyric Acid Anhydrides In a 1,000-ml-multi-neck flask with dephlegmator (partial condenser) and distillation bridge, 25 g of an (R)/(S)-3-hydroxybutyric acid (3-BHB) are provided in 95 g acetic acid. 90 g acetic anhydride are added dropwise to the reaction mixture at 80° C. under $N_2$ atmosphere over the course of one hour. The reaction mixture is stirred at 80° C. for another 4 to 5 h. 3 g of a medium-chain mono-/diglyceride ($C_8/C_{10}$ fatty acid with the ratio 60%/40%; glyceride distribution:monoester 30 to 70%, di-ester 10 to 30%, tri-ester 1 to 5%) are added to the reaction mixture at 80° C. and stirred for 4 to 5 h. The resulting 3-acetoxybutyric acid or acetic acid is distilled off under vacuum (<50 mbar) at 100 to 120° C.

The reaction product is a MCF/3-acetoxy-BHB triglyceride.

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 5

Production of Mixed Long Chain Fatty Acid (LCFA) and 3-Acetoxybutyric Acid (Ac-BHB) Triglycerides from Partial Glycerides and 3-Acetoxybutyric Acid Anhydrides In a 1,000-ml-multi-neck flask with dephlegmator (partial condenser) and distillation bridge, 500 g of a long-chain, refined, bleached and deodorized fish oil (EPA/DHA content 20 to 50%, ratio 50:50) are selectively cleaved with 250 g water 0.4 g enzyme lipase at 40° C. under stirring and $N_2$-atmosphere for 8 to 12 h. Mainly fatty acids<$C_{20}$ are split off. The phases are then separated and the organic phase filtered. The organic phase consists of free fatty acids (mainly <$C_{20}$) and mono-, di- and triglycerides of LCFA (>$C_{20}$). The free fatty acids (<$C_{20}$) are distilled off from the reaction mixture by short path distillation under vacuum and at temperatures of 140 to 180° C. A mixture of mono-, di- and triglycerides of LCFA (>$C_{20}$) is obtained.

In a 1,000-ml-multi-neck flask with dephlegmator (partial condenser) and distillation bridge, 25 g of an (R)/(S)-3-hydroxybutyric acid (3-BHB) are provided in 95 g acetic acid. 90 g acetic anhydride are added dropwise to the reaction mixture at 80° C. under $N_2$-atmosphere in the course of one hour. The reaction mixture is stirred at 80° C. for another 4 to 5 h. 2 g of the above mixture of mono-, di- and triglycerides of LCFA (>$C_{20}$) are added to the reaction mixture at 80° C. and stirred for 4 to 5 h. The resulting 3-acetoxybutyric acid or acetic acid is distilled off under vacuum (<50 mbar) at 100 to 120° C.

The reaction product is an LCF/acetyl-BHB triglyceride (3-acetoxy-BHB triglyceride).

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 6

Preparation of Mixed Long Chain Fatty Acid (LCFA). Medium Chain Fatty Acid (MCFA) and 3-Acetoxybutyric Acid (Ac-BHB) Triglycerides from Partial Glycerides and 3-Acetoxybutyric Acid Anhydrides In a 1,000-ml-multi-neck flask with dephlegmator (partial condenser) and distillation bridge, 500 g of a long-chain, refined, bleached and deodorized fish oil (EPA/DHA content 20 to 50%, ratio 50:50) are selectively cleaved with 250 g water 0.4 g enzyme lipase at 40° C. under stirring and $N_2$-atmosphere for 8 to 12 h. Mainly fatty acids<$C_{20}$ are split off. The phases are then separated and the organic phase filtered. The organic phase consists of free fatty acids (mainly <$C_{20}$) and mono-, di- and triglycerides of LCFA (>$C_{20}$). The free fatty acids (<$C_{20}$) are distilled off from the reaction mixture by short path distillation under vacuum and at temperatures of 140 to 180° C. A mixture of mono-, di- and triglycerides of LCFA (>$C_{20}$) is obtained.

In a 1,000-ml-multi-neck flask with dephlegmator (partial condenser) and distillation bridge, 25 g of an (R)/(S)-3-hydroxybutyric acid (3-BHB) are provided in 95 g acetic acid. 90 g acetic anhydride are added dropwise to the reaction mixture at 80° C. under $N_2$-atmosphere within the course of one hour. The reaction mixture is stirred at 80° C. for another 4 to 5 h. 30 g of the mixture prepared above of mono-, di- and triglycerides of LCFA (>$C_{20}$) and 7.5 g of a medium-chain mono-/di-glyceride ($C_8$/$C_{10}$ fatty acids, ratio 60%/40%; glyceride distribution:mono-esters 30 to 70%, di-esters 10 to 30%, tri-esters 1 to 5%) are added to the reaction mixture at 80° C. and stirred for 4 to 5 h. The resulting 3-acetoxybutyric acid is distilled off under vacuum (<50 mbar) at 100 to 120° C. The remaining reaction product is now randomized with immobilized enzyme (CALB) at 40° C. under stirring and $N_2$-atmosphere for 8 to 12 h.

The reaction product is an LCF/MCF/acetyl-BHB triglyceride (3-acetoxy-BHB triglyceride).

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 7

Production of Mixed Long Chain Fatty Acid (LCFA). Medium Chain Fatty Acid (MCFA) and 3-Hydroxybutyric Acid (3-BHB) Triglycerides from Partial Glycerides In a 1,000-ml-multi-neck flask with dephlegmator (partial condenser) and distillation bridge, 500 g of a long-chain, refined, bleached and deodorized fish oil (EPA/DHA content 20 to 50%, ratio 50:50) are selectively cleaved with 250 g water 0.4 g enzyme lipase at 40° C. under stirring and $N_2$-atmosphere for 8 to 12 h. Mainly fatty acids<$C_{20}$ are split off. The phases are then separated and the organic phase is filtered. The organic phase consists of free fatty acids (mainly <$C_{20}$) and mono-, di- and triglycerides of LCFA (>$C_{20}$). The free fatty acids (<$C_{20}$) are distilled off from the reaction mixture by short path distillation under vacuum and at temperatures of 140 to 180° C. A mixture of mono-, di- and triglycerides of LCFA (>$C_{20}$) is obtained.

In a 250-ml-multi-neck flask with dephlegmator (partial condenser) and distillation bridge, 50 g of the mixture prepared above of mono-, di- and triglycerides of LCFA (>$C_{20}$), 25 g of a medium-chain mono-, diglyceride ($C_8$/$C_{10}$ fatty acids ratio 60%/40%; glyceride distribution:mono-ester 30 to 70%, di-ester 10 to 30%, triglyceride 1 to 5%) and 35 g of (R)/(S)-3-hydroxybutyric acid ethyl ester (3-BHB ethyl ester) are transesterified at 50 to 70° C. under vacuum (<500 mbar) by means of 0.85 g immobilized enzyme (CALB).

The reaction product is an LCF/MCF/3-BHB triglyceride.

Cleavage experiments (cleavage tests) of this reaction product in a gastric or intestinal medium (FaSSGF medium, which simulates the stomach, or FaSSIF medium, which simulates the intestinal tract), in each case in the presence or absence of pancreatin, demonstrate the cleavage to 3-BHB in free form. These cleavage experiments prove that lipids comprising structural units based on glycerides of 3-hydroxybutyric and/or 3-alkoxybutyric acids (here specifically the reaction product obtained) are efficient precursors or metabolites of free 3-hydroxybutyric acid or its salts, especially with regard to their intended effect, which are also present in physiologically compatible form.

Example 8

Preparation of 3-Acetoxybutyric Acid Ethyl Ester (3-Ac-BHB Ethyl Ester) and Subsequent Reaction In a 250-ml-multi-neck flask with dephlegmator (partial condenser) and distillation bridge, 50 g (R)/(S)-3-hydroxybutyric acid ethyl ester (racemic 3-BHB ethyl ester) and 55 g acetic anhydride are provided. The reaction mixture is reacted at 100° C. under stirring and under reflux for 10 h. The acetic acid and excess acetic anhydride are then distilled off under vacuum. A 3-acetoxybutyric acid ethyl ester with 98% purity is obtained. The characterization is done by gas chromatography (GC) and GC-MS analysis (gas chromatography with mass spectrometry coupling). The results of the turnover/time curve are summarized in the following table.

| time/h | acetic anhydride/ % | 3-BHB-ethyl ester/% | 3-Ac-BHB-ethyl ester (product)/ % | unknown/ % | comment |
|---|---|---|---|---|---|
| 1 | 28.8 | 38.9 | 31.3 | 1 | 80° C. |
| 3 | 23.1 | 26.1 | 49.5 | 1.3 | — |
| 6 | 18.6 | 15.9 | 63.9 | 1.6 | Temperature increase to 100° C. |
| 9 | 12.4 | 3.2 | 82.6 | 1.8 | — |
| 12 | 11.5 | 1.3 | 85.6 | 1.6 | — |
| — | 0 | 0.6 | 97.7 | 1.7 | after distillation |

The further conversion of 3-acetoxybutyric acid ethyl ester (3-Ac-BHB ethyl ester) and application tests are described below: Furthermore, it can be shown that the 3-acetoxybutyric acid ethyl ester obtained in this way can be used as a starting material in a transesterification with enzyme as catalyst (e.g. immobilized enzyme, such as CALB lipase on polymer support, derived from *Candida antarctica*, e.g. e.g. Novozym® 435 from Sigma-Aldrich or Merck or Lipozym® 435 from Strem Chemicals, Inc.) to glycerides (reaction at 50 to 70° C., 24 h 1 wt.-% enzyme). Triacetin is used as a further starting material; since it already contains acetyl groups, no undesired by-products are formed during any transesterification on the already acetylated OH-group of the 3-BHB ethyl ester. Only ethyl acetate is formed as a by-product, which can be easily removed. A mixture of mono-, di- and triglycerides of 3-acetoxybutyric acid is formed. This product is an analogue or model substance of the products according to the invention.

Cleavage experiments (cleavage tests) of this mixture in a gastric or intestinal medium (FaSSGF medium simulating the stomach or FaSSIF medium simulating the intestinal tract), in each case in the presence or absence of pancreatin, demonstrate the cleavage to 3-BHB in free form (cleavage cascade from triglyceride via diglyceride to monoglyceride to free 3-BHB). These cleavage experiments prove that also the glycerides of the blocked 3-hydroxybutyric acid or its salts are efficient precursors or metabolites of free hydroxybutyric acid or its salts, especially with regard to their intended effect, which are also present in a physiologically compatible form.

Example 9

Further Manufacturing Examples: Carboxylic Acid Anhydride Synthesis (Educt)

According to the described carboxylic acid anhydride production method, the carboxylic acid anhydrides of heptanoic acid ($C_7$ acid), lauric acid ($C_{12}$ acid) and oleic acid ($C_{18}$ acid) are first produced.

To prepare the carboxylic anhydride of heptanoic acid ($C_7$ acid), 860 g of heptanoic acid are placed in a 2,000-ml-multi-neck flask with dephlegmator (partial condenser) and distillation bridge and 445 g of acetic anhydride are added at 90° C. under stirring. The reaction mixture is then reacted at 130° C. under reflux for 6 h under stirring. The acetic acid and excess acetic anhydride are then distilled off under vacuum. The heptanoic anhydride is obtained. The characterization is performed by GC and GC-MS.

The carboxylic acid anhydrides of lauric acid ($C_{12}$ acid) and oleic acid ($C_{18}$ acid) are produced in the same way.

Subsequently—corresponding to the production of 3-acetoxybutyric acid ethyl ester described above—the relevant carboxylic acid anhydride is reacted with 3-BHB ethyl ester, so that the 3-BHB ethyl ester capped with the carboxylic acid anhydride in the 3-position results. These can be used as educts in the described syntheses.

Physiological Application Tests: In-Vitro Digestion Tests

Digestion Experiments (Splitting or Cleavage Experiments) of Inventive Compounds By means of cleavage experiments it is shown that reaction products or their mixtures (reaction products from the previous examples 1 to 7) produced according to the invention can be cleaved in the human gastrointestinal tract. The reaction products from the examples 1 to 7, obtained and purified as described above, are subjected to the cleavage experiments described below.

For the cleavage experiments under near-body conditions two media are investigated:

FaSSGF, which simulates the stomach
FaSSIF, which simulates the intestinal tract Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that all samples hydrolyze under FaSSGF conditions with Panzytrat® and without Panzytrat®; this is mainly due to the low pH value (pH=1.6). Under FaSSIF conditions, a lower conversion using Panzytrat® takes place.

All experiments show that the desired free acid 3-BHB is generated. The conversion/time course of the aqueous cleavage of the compounds according to the invention, including the increase in acid number over time, proves the desired decomposition of the educts to the free acid (3-BHB). This is confirmed by appropriate analysis.

The previously described cleavage experiments prove that the lipids comprising structural units based on glycerides of 3-hydroxybutyric acids and/or 3-alkoxybutyric acids are efficient precursors or metabolites of free hydroxybutyric acid or its salts, especially with regard to their intended effect, and are also present in a physiologically compatible form.

The invention claimed is:

1. A method for producing lipids comprising structural units based on glycerides of at least one of 3-hydroxybutyric acid and 3-alkoxybutyric acid, wherein at least one glyceride of the general formula (I)

$$R^1O-CH_2-CH(OR^2)-CH_2-OR^3 \quad (I)$$

wherein in the general formula (I) the radicals $R^1$, $R^2$ and $R^3$, identical or different, each independently of one another represent,
hydrogen,
a radical $C_1$-$C_{11}$-alkyl-C(O)—,
a radical $C_{12}$-$C_{29}$-alkyl-C(O)—,
however, with the proviso that at least one of the radicals $R^1$, $R^2$ and $R^3$ does not represent hydrogen,
is reacted with at least one 3-hydroxybutyric acid, 3-alkoxybutyric acid and their derivatives of the general formula (II)

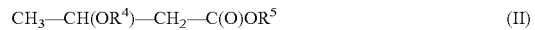

$$CH_3-CH(OR^4)-CH_2-C(O)OR^5 \quad (II)$$

wherein in the general formula (II)
the radical $R^4$ represents hydrogen or a radical $C_1$-$C_{30}$-alkyl-C(O)—,
the radical $R^5$ represents hydrogen or $C_1$-$C_4$-alkyl,
wherein the reaction is carried out in the absence of any solvents and
wherein the reaction is carried out in the presence of an enzyme as a catalyst,
so that, as a reaction product, there is obtained a mixture of at least two different lipids comprising structural units based on glycerides of at least one of 3-hydroxybutyric acid and 3-alkoxybutyric acid of the general formula (III)

$$R^6O-CH_2-CH(OR^7)-CH_2-OR^8 \quad (III)$$

wherein in the general formula (III) the radicals $R^6$, $R^7$ and $R^8$, identical or different, each independently of one another represent
a radical $C_1$-$C_{11}$-alkyl-C(O)—,
a radical $C_{12}$-$C_{29}$-alkyl-C(O)—,
a radical $CH_3-CH(OR^4)-CH_2-C(O)$—, wherein the radical $R^4$ has the meaning defined hereinabove, however, with the proviso that one or two of the radicals $R^6$, $R^7$ and $R^8$ represents a radical $CH_3$—$CH(OR^4)$—$CH_2$—$C(O)$—.

2. The method according to claim 1,
wherein the catalyst is recycled after the reaction; and
wherein the enzyme is selected from the group consisting of synthetases, catalases, esterases, lipases and combinations thereof.

3. The method according to claim 1,
wherein the enzyme is derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof; and
wherein the enzyme is used in immobilized form on a carrier; and
wherein the enzyme is recycled after the reaction.

4. The method according to claim 1,
wherein the enzyme is used in amounts, based on the total amount of starting compounds (I) and (II), in the range of from 0.001% by weight to 20% by weight.

5. The method according to claim 1,
wherein, in the case that in general formula (II) the radical $R^5$ denotes hydrogen, the anhydride of the general formula (IIa)

$$[CH_3-CH(OR^4)-CH_2-C(O)]_2O \quad \text{(IIa)}$$

wherein in the general formula (IIa) the radical $R^4$ has the meaning defined hereinabove,
is used instead of the free acid.

* * * * *